(12) United States Patent
Kirkpatrick et al.

(10) Patent No.: US 10,994,089 B2
(45) Date of Patent: *May 4, 2021

(54) BRIDLE DELIVERY SYSTEM, METHOD, AND APPARATUS FOR SECURING NASAL TUBES

(71) Applicant: Avent, Inc., Alpharetta, GA (US)

(72) Inventors: Donald R. Kirkpatrick, Hawthorn Woods, IL (US); Crystal Koelper, North Barrington, IL (US); Jill Lazar, Highland Park, IL (US); Michael Masino, Lake in the Hills, IL (US); Shawn Purnell, Sandy Springs, GA (US); Michael C. Shaughnessy, Arlington Heights, IL (US); Stephanie Wasielewski, Arlington Heights, IL (US)

(73) Assignee: Avent, Inc., Alpharetta, GA (US)

( * ) Notice: Subject to any disclaimer, the term of this patent is extended or adjusted under 35 U.S.C. 154(b) by 218 days.

This patent is subject to a terminal disclaimer.

(21) Appl. No.: 15/936,993

(22) Filed: Mar. 27, 2018

(65) Prior Publication Data

US 2018/0214652 A1 Aug. 2, 2018

Related U.S. Application Data

(63) Continuation of application No. 14/096,758, filed on Dec. 4, 2013, now Pat. No. 9,956,366.

(Continued)

(51) Int. Cl.
*A61M 16/04* (2006.01)
*A61M 25/01* (2006.01)
(Continued)

(52) U.S. Cl.
CPC .... *A61M 16/0497* (2013.01); *A61M 16/0461* (2013.01); *A61M 16/0488* (2013.01);
(Continued)

(58) Field of Classification Search
CPC .............. A61M 16/00; A61M 16/0461; A61M 16/0488; A61M 16/0497; A61M 16/0666;
(Continued)

(56) References Cited

U.S. PATENT DOCUMENTS 4,480,639 A    11/1984   Peterson et al.
4,634,425 A *   1/1987   Meer ................... A61J 15/0003
                                                                      128/207.18

(Continued)

FOREIGN PATENT DOCUMENTS

EP         0 609 020 A1    8/1994
WO       WO 92/17150     10/1992
(Continued)

OTHER PUBLICATIONS

Definition of Integrally by Merriam-Webster; www.merriam-webster.com/dictionary/integrally; retrieved 2020. (Year: 2020).*

(Continued)

*Primary Examiner* — Colin W Stuart
(74) *Attorney, Agent, or Firm* — Dority & Manning, P.A.

(57) ABSTRACT

Systems, methods, and apparatus for securing nasal tubes are disclosed. An exemplary system includes a bridle, a magnetic portion connected to the bridle, a delivery probe, a retrieval probe, and a clamp. The delivery probe includes an elongated member having proximal and distal ends, the distal end configured to deliver the magnetic portion, and a bridle lock configured to release the bridle upon actuation of an actuator. The retrieval probe includes an elongated member having proximal and distal ends, the distal end including a magnetic portion configured to magnetically couple with (Continued)

the other magnetic portion, and a magnetic coupling indicator configured to provide an indication in response to a magnetic coupling. The clamp includes a channel portion with an inside diameter larger than an outside diameter of a nasal tube. The clamp is configured to secure the nasal tube following placement of the bridle by the delivery and retrieval probes.

25 Claims, 8 Drawing Sheets

Related U.S. Application Data (60) Provisional application No. 61/752,304, filed on Jan. 14, 2013.

(51) Int. Cl.
*A61M 25/02* (2006.01)
*A61M 16/08* (2006.01)
*A61M 16/06* (2006.01)

(52) U.S. Cl.
CPC ........ *A61M 25/01* (2013.01); *A61M 25/0127* (2013.01); *A61M 25/02* (2013.01); *A61M 16/0666* (2013.01); *A61M 16/0816* (2013.01); *A61M 2025/024* (2013.01); *A61M 2025/0213* (2013.01); *A61M 2025/0226* (2013.01); *A61M 2210/0618* (2013.01)

(58) Field of Classification Search
CPC .......... A61M 16/0683; A61M 16/0688; A61M 25/00; A61M 25/005; A61M 25/01; A61M 25/02; A61M 2025/0213; A61M 2025/0226; A61M 2025/024; A61M 2025/022; A61M 2025/0246; A61M 2025/0253; A61M 2210/0618; A61M 25/0127

See application file for complete search history.

(56) References Cited

U.S. PATENT DOCUMENTS

| | | | |
|---|---|---|---|
| 4,778,448 A * | 10/1988 | Meer | A61J 15/003 128/207.18 |
| 4,836,214 A | 6/1989 | Sramek | |
| 4,921,481 A | 5/1990 | Danis et al. | |
| 5,185,005 A | 2/1993 | Ballantyne | |
| 5,399,165 A | 3/1995 | Paul, Jr. | |
| 5,660,168 A | 8/1997 | Ottosson et al. | |
| 6,334,064 B1 | 12/2001 | Fiddian-Green | |
| 6,357,447 B1 | 3/2002 | Swanson et al. | |
| 6,464,668 B1 * | 10/2002 | Pace | A61M 25/02 604/179 |
| 6,631,715 B2 | 10/2003 | Kirn | |
| 6,837,237 B2 | 1/2005 | Kirn | |
| 6,929,635 B2 | 8/2005 | Shelso | |
| 7,534,228 B2 | 5/2009 | Williams | |
| 7,818,155 B2 | 10/2010 | Stuebe et al. | |
| 8,147,486 B2 | 4/2012 | Honour et al. | |
| 8,177,773 B2 | 5/2012 | Ovcharchyn et al. | |
| 8,613,702 B2 | 12/2013 | Feer et al. | |
| 8,986,230 B2 | 3/2015 | Nishtala | |
| 9,179,971 B2 | 11/2015 | Kirschenman | |
| 9,226,878 B2 | 1/2016 | Elia et al. | |
| 9,295,395 B2 | 3/2016 | Elia et al. | |
| 9,302,074 B2 | 4/2016 | Atkinson et al. | |
| 9,532,739 B2 | 1/2017 | Bennett-Guerrero | |
| 9,610,227 B2 | 4/2017 | Elia | |
| 9,642,779 B2 | 5/2017 | Elia et al. | |
| 9,713,579 B2 | 7/2017 | Elia et al. | |
| 9,956,366 B2 * | 5/2018 | Kirkpatrick | A61M 25/0127 |
| 2004/0069309 A1 | 4/2004 | Kirn | |
| 2005/0236001 A1 | 10/2005 | Williams | |
| 2008/0097179 A1 | 4/2008 | Russo | |
| 2008/0167607 A1 | 7/2008 | Pfeiffer et al. | |
| 2008/0215002 A1 | 9/2008 | Rozenberg et al. | |
| 2008/0249467 A1 | 10/2008 | Burnett et al. | |
| 2010/0145147 A1 | 6/2010 | Pinsky et al. | |
| 2010/0294271 A1 | 11/2010 | Pittaway et al. | |
| 2012/0016256 A1 | 1/2012 | Mabary et al. | |
| 2012/0277619 A1 | 11/2012 | Starkebaum et al. | |
| 2013/0225946 A1 | 8/2013 | Feer et al. | |
| 2014/0041666 A1 * | 2/2014 | Slaga | A61M 16/0461 128/207.18 |
| 2016/0113843 A1 | 4/2016 | Elia et al. | |
| 2016/0129223 A1 | 5/2016 | Kirschenman | |
| 2016/0331298 A1 | 11/2016 | Burnett et al. | |
| 2017/0071502 A1 | 3/2017 | Bennett-Guerrero | |
| 2017/0202750 A1 | 7/2017 | Elia | |
| 2018/0078195 A1 | 3/2018 | Sutaria et al. | |
| 2018/0161249 A1 | 6/2018 | Elia et al. | |
| 2018/0289536 A1 | 10/2018 | Burnett | |

FOREIGN PATENT DOCUMENTS

| | | |
|---|---|---|
| WO | WO 2008/010039 A2 | 1/2008 |
| WO | WO 2009/029869 A2 | 3/2009 |

OTHER PUBLICATIONS

International Search Report and Written Opinion dated Mar. 3, 2014 for corresponding International Appln. No. PCT/US2013/073144.

* cited by examiner

BRIDLE DELIVERY SYSTEM, METHOD, AND APPARATUS FOR SECURING NASAL TUBES

CROSS REFERENCE TO RELATED APPLICATIONS

The present application is a continuation of U.S. patent application Ser. No. 14/096,758, filed on Dec. 4, 2013, which claims the benefit of, and priority to, U.S. Provisional Patent Application Ser. No. 61/752,304, filed on Jan. 14, 2013, the entire content of each of which is incorporated by reference herein. The present application relates to the following co-owned patents and pending patent applications: "Catheter Locator Apparatus And Method Of Use," filed on Dec. 23, 2009, as U.S. patent application Ser. No. 12/646,263, issued on Sep. 11, 2012, as U.S. Pat. No. 8,265,732; "Catheter Locator Apparatus And Method Of Use," filed on Aug. 9, 2012, as U.S. patent application Ser. No. 13/570,999; "Tubing Assembly And Signal Generator Placement Control Device And Method For Use With Catheter Guidance Systems," filed on Jan. 13, 2005, as U.S. patent application Ser. No. 11/036,514, issued on Jul. 12, 2011, as U.S. Pat. No. 7,976,518; and "Tubing Assembly And Signal Generator Placement Control Device And Method For Use With Catheter Guidance Systems," filed on Jun. 2, 2011, as U.S. patent application Ser. No. 13/151,882, the entire content of each of which is incorporated by reference herein.

TECHNICAL FIELD

The present disclosure relates in general to a system, method, and apparatus for securing nasal tubes, and more specifically to a magnetic bridle delivery system for securing nasal tubes with a clamp.

BACKGROUND

The use of nasal tubes is commonly required in a medical setting, and many methods of securing nasal tubes that have been placed are known in the art. Generally, a nasal tube which has been inserted into a nostril may extend into a patient's stomach, intestinal tract, or lungs. Typically, once the nasal tube is in place, it is important to secure the tube. It should be appreciated that failing to properly secure a nasal tube can result in a dangerous situation for a patient, as well as increasing the cost of care, for example, by requiring repositioning of the nasal tube and re-securing the nasal tube. There are various existing systems and methods for securing a nasal tube. For example, a nasal tube may be secured using a bridle being placed around the vomer bone. A clinician may place the bridle using a long flexible member, such as a tube, including the bridle and a magnet at the distal end, which is held together by the clinician's grasp. The long flexible member is inserted into one nostril, into the naval cavity towards the rear of the vomer bone. A probe with a magnet at the distal end is inserted into the other nostril to allow the magnets to contact each other around the vomer bone. Once the magnets have made contact, the clinician lets go of the bridle to allow the long flexible member to enter the nostril, and the probe is pulled outward, which pulls the long flexible member including the bridle around the vomer bone. With the bridle looped around the vomer bone and extending from both nostrils, the bridle may be secured with a clamp, which may have a channel to accept the nasal tube to secure the nasal tube. For example, the channel has a smaller inside diameter than the outside diameter of the nasal tube, which provides for a tight fit of the nasal tube in the channel and allows the nasal tube to not fall out of the clamp prior to closing the clamp. The clinician may bring the clamp as close to the nostril as possible and press the tube into the tight channel in the clamp, place the bridle into the clamp, and close the clamp to secure the nasal tube to the bridle. However, the current systems and methods employed in the prior art for placing a bridle and securing a nasal tube may be improved upon as presently disclosed.

SUMMARY

The present disclosure provides a new and innovative system, method, and apparatus for securing nasal tubes. An exemplary system includes a bridle, a magnetic portion connected to the bridle, a delivery probe, a retrieval probe, and a clamp. The delivery probe includes an elongated member having proximal and distal ends, the distal end configured to deliver the magnetic portion, and a bridle lock configured to release the bridle upon actuation of an actuator. The retrieval probe includes an elongated member having proximal and distal ends, the distal end including a magnetic portion configured to magnetically couple with the other magnetic portion, and a magnetic coupling indicator configured to provide an indication in response to a magnetic coupling. The clamp includes a channel portion with an inside diameter larger than an outside diameter of a nasal tube. The clamp is configured to secure the nasal tube following placement of the bridle by the delivery and retrieval probes.

In accordance with an exemplary aspect of the present disclosure, a system for securing a nasal tube comprises: a bridle; a first magnetic portion connected to the bridle; a delivery probe including: a first elongated member having a first proximal end and a first distal end, the first distal end being configured to deliver the first magnetic portion; and a bridle lock with an actuator coupled to the first proximal end, the bridle lock configured to release the bridle upon actuation of the actuator; a retrieval probe including: a second elongated member having a second proximal end and a second distal end, the second distal end including a second magnetic portion configured to magnetically couple with the first magnetic portion; and a magnetic coupling indicator configured to provide an indication in response to the first magnetic portion and the second magnetic portion being magnetically coupled; and a clamp including a channel portion with an inside diameter larger than an outside diameter of the nasal tube, the clamp configured to secure the nasal tube.

In accordance with another exemplary aspect of the present disclosure, which may be used in combination with any one or more of the preceding aspects, a system for securing a nasal tube comprises: a bridle; a first magnetic portion connected to the bridle; a delivery probe including: a first elongated member having a first proximal end and a first distal end, the first distal end being configured to deliver the first magnetic portion; and a bridle lock with an actuator coupled to the first proximal end, the bridle lock configured to release the bridle upon actuation of the actuator; and a retrieval probe including a second elongated member having a second proximal end and a second distal end, the second distal end including a second magnetic portion configured to magnetically couple with the first magnetic portion.

In accordance with another exemplary aspect of the present disclosure, which may be used in combination with any one or more of the preceding aspects, a system for securing a nasal tube comprises: a bridle; a first magnetic portion connected to the bridle; and a delivery probe including: a first elongated member having a first proximal end and a first distal end, the first distal end being configured to deliver the first magnetic portion to a retrieval probe including a second elongated member having a second proximal end and a second distal end, the second distal end including a second magnetic portion configured to magnetically couple with the first magnetic portion; and a bridle lock with an actuator coupled to the first proximal end, the bridle lock configured to release the bridle upon actuation of the actuator.

In accordance with another exemplary aspect of the present disclosure, which may be used in combination with any one or more of the preceding aspects, an apparatus for securing a nasal tube comprises: a first elongated member having a first proximal end and a first distal end, the first distal end being configured to deliver a first magnetic portion to a retrieval probe including a second elongated member having a second proximal end and a second distal end, the second distal end including a second magnetic portion configured to magnetically couple with the first magnetic portion; and a bridle lock with an actuator coupled to the first proximal end, the bridle lock configured to release a bridle upon actuation of the actuator.

In accordance with another exemplary aspect of the present disclosure, which may be used in combination with any one or more of the preceding aspects, an apparatus for securing a nasal tube comprises: a second elongated member having a second proximal end and a second distal end, the second distal end including a second magnetic portion configured to receive a first magnetic portion from a delivery probe including a first elongated member having a first proximal end and a first distal end, the first distal end being configured to magnetically couple with the second magnetic portion; and a magnetic coupling indicator configured to provide an indication in response to the first magnetic portion and the second magnetic portion being magnetically coupled.

In accordance with another exemplary aspect of the present disclosure, which may be used in combination with any one or more of the preceding aspects, a method for securing a nasal tube comprises: inserting a delivery probe into a first nostril, the delivery probe including a first elongated member having a first proximal end and a first distal end, the first distal end being configured to deliver a first magnetic portion which is connected to a bridle; inserting a retrieval probe into a second nostril, the retrieval probe including a second elongated member having a second proximal end and a second distal end, the second distal end including a second magnetic portion configured to magnetically couple with the first magnetic portion; actuating an actuator on a bridle lock at the first proximal end to release the bridle; removing the retrieval probe from the second nostril and the delivery probe from the first nostril, such that the bridle extends into the first nostril and out of the second nostril; inserting the nasal tube into a clamp with the bridle; and clamping the nasal tube and the bridle.

In accordance with another exemplary aspect of the present disclosure, which may be used in combination with any one or more of the preceding aspects, the first elongated member is a catheter.

In accordance with another exemplary aspect of the present disclosure, which may be used in combination with any one or more of the preceding aspects, the first elongated member includes a stylet, and the first elongated member is a first length from the first proximal end to the first distal end, and the stylet extends from the first proximal end toward the first distal end for a second length which is less than the first length.

In accordance with another exemplary aspect of the present disclosure, which may be used in combination with any one or more of the preceding aspects, the first elongated member is configured to adjustably curve over a third length of the first elongated member beyond the second length when a tension is applied to the bridle and maintained by the bridle lock.

In accordance with another exemplary aspect of the present disclosure, which may be used in combination with any one or more of the preceding aspects, at least one of the first elongated member and the second elongated member is a flexible tube.

In accordance with another exemplary aspect of the present disclosure, which may be used in combination with any one or more of the preceding aspects, at least one of the first elongated member and the second elongated member includes an integrally formed coil.

In accordance with another exemplary aspect of the present disclosure, which may be used in combination with any one or more of the preceding aspects, at least one of the first elongated member and the second elongated member includes a stylet.

In accordance with another exemplary aspect of the present disclosure, which may be used in combination with any one or more of the preceding aspects, the stylet is configured to be adjusted to varying lengths.

In accordance with another exemplary aspect of the present disclosure, which may be used in combination with any one or more of the preceding aspects, a magnetic coupling of the first magnetic portion and the second magnetic portion is a face to face magnetic coupling.

In accordance with another exemplary aspect of the present disclosure, which may be used in combination with any one or more of the preceding aspects, at least one of the first magnetic portion and the second magnetic portion includes a rare earth magnet.

In accordance with another exemplary aspect of the present disclosure, which may be used in combination with any one or more of the preceding aspects, at least one of the first magnetic portion and the second magnetic portion includes a permanent magnet.

In accordance with another exemplary aspect of the present disclosure, which may be used in combination with any one or more of the preceding aspects, at least one of the first magnetic portion and the second magnetic portion includes at least one of a cylindrical magnet and a ring magnet.

In accordance with another exemplary aspect of the present disclosure, which may be used in combination with any one or more of the preceding aspects, the first magnetic portion is inflexible.

In accordance with another exemplary aspect of the present disclosure, which may be used in combination with any one or more of the preceding aspects, the first magnetic portion includes only a magnet.

In accordance with another exemplary aspect of the present disclosure, which may be used in combination with any one or more of the preceding aspects, the first magnetic portion is over-molded to include a portion of the bridle.

In accordance with another exemplary aspect of the present disclosure, which may be used in combination with any one or more of the preceding aspects, at least one of the delivery probe and the retrieval probe include a magnetic coupling indicator configured to provide an indication in response to the first magnetic portion and the second magnetic portion being magnetically coupled.

In accordance with another exemplary aspect of the present disclosure, which may be used in combination with any one or more of the preceding aspects, the magnetic coupling indicator is a light emitting diode.

In accordance with another exemplary aspect of the present disclosure, which may be used in combination with any one or more of the preceding aspects, the clamp is a hingeless monolithic clamp.

In accordance with another exemplary aspect of the present disclosure, which may be used in combination with any one or more of the preceding aspects, the clamp includes two pressure bars on opposing sides of the channel portion.

In accordance with another exemplary aspect of the present disclosure, which may be used in combination with any one or more of the preceding aspects, a minimum clearance between opposing sides of the clamp is greater than or substantially equal to an outside diameter of the nasal tube.

In accordance with another exemplary aspect of the present disclosure, which may be used in combination with any one or more of the preceding aspects, the clamp includes a plurality of channels for at least two different size nasal tubes.

In accordance with another exemplary aspect of the present disclosure, which may be used in combination with any one or more of the preceding aspects, the bridle is released in response to a magnetic coupling indicator providing an indication in response to the first magnetic portion and the second magnetic portion being magnetically coupled.

In accordance with another exemplary aspect of the present disclosure, which may be used in combination with any one or more of the preceding aspects, the clamp includes a channel portion with an inside diameter larger than an outside diameter of the nasal tube.

In accordance with another exemplary aspect of the present disclosure, which may be used in combination with any one or more of the preceding aspects, method for securing a nasal tube further comprises: sliding the channel portion along the nasal tube into a first position before clamping the nasal tube and the bridle.

Additional features and advantages of the disclosed system, method, and apparatus are described in, and will be apparent from, the following Detailed Description and the Figures.

DETAILED DESCRIPTION OF EXAMPLE EMBODIMENTS

Figure 1A:
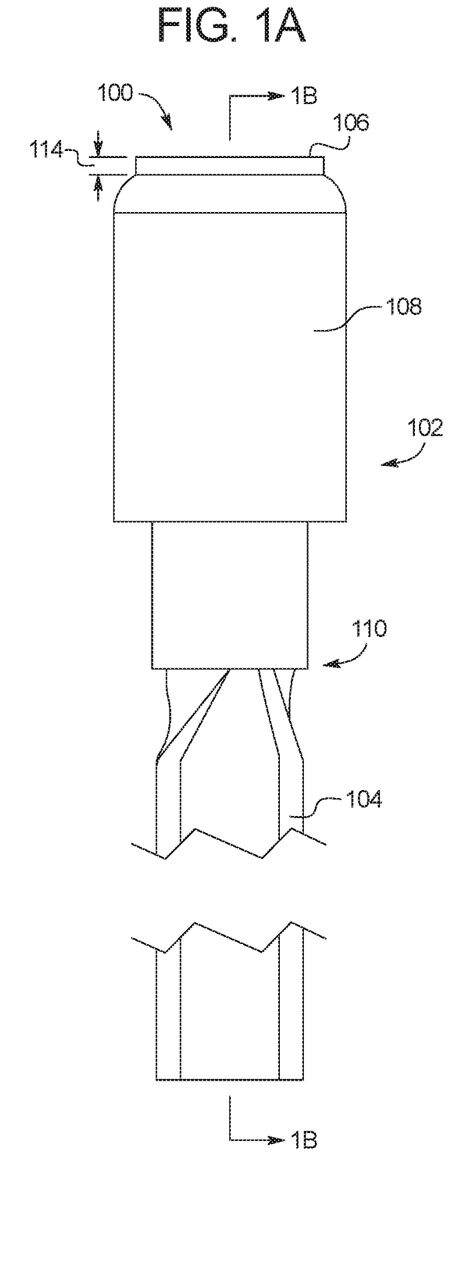
FIG. 1A is a perspective view of an example bridle assembly, according to an example embodiment of the present disclosure.
Figure 1B:
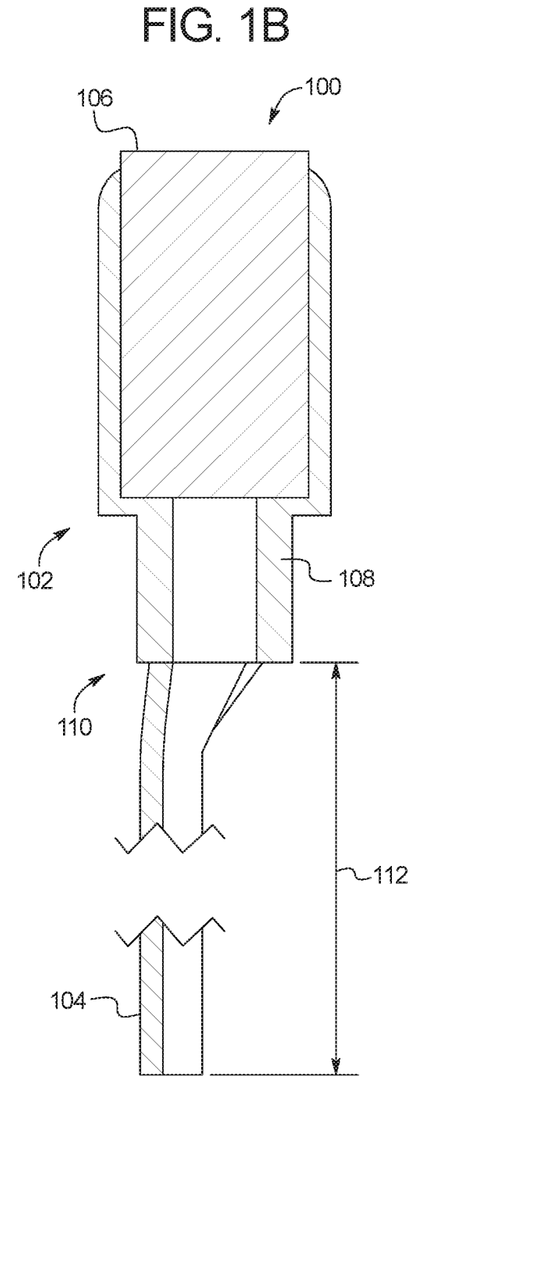
FIG. 1B is a cross-sectional view of an example bridle assembly, according to an example embodiment of the present disclosure.

A perspective view of an example bridle assembly 100 is illustrated in FIG. 1A. The illustrated bridle assembly 100 includes a magnetic portion 102 connected to a bridle 104. The magnetic portion 102 includes a magnet 106 which is held inside a magnet holding tip 108. A cross-sectional view of the bridle assembly 100 is illustrated in FIG. 1B, taken along line 1B-1B of FIG. 1A. In an example embodiment, the bridle 104 is made of an umbilical tape that is approximately one eighth inch wide by 24 inches long. The bridle 104 may be integrally attached to the magnet holding tip 108 at bridle connection point 110, where as illustrated, the width of the bridle 104 curves around the bottom of magnet holding tip 108 in FIG. 1A, and has a length 112 (e.g., 24 inches) as indicated in FIG. 1B. The magnet 106 may be a cylindrical rare earth magnet. In an example embodiment, the magnet may be a permanent magnet in any of a variety of shapes, such as ring magnet. The magnet holding tip 108 may be molded plastic which is sized to accept the magnet 106 to slightly extend outward from the end of the magnetic holding tip 108, as shown in FIG. 1A as protruding magnet portion 114. In an example embodiment, the magnet 106 may be flush with the top of the magnetic holding tip 108, or may extend to a greater degree or a lesser degree. In an example embodiment, the bridle 104 may be over-molded into the magnetic holding tip 108. Also, the magnet 106, the bridle 104, and the magnetic holding tip 108 may be secured with an adhesive or other suitable fastening means to ensure the bridle 104 and magnet 106 are operatively coupled for delivery into the nasal cavity.

Figure 2:
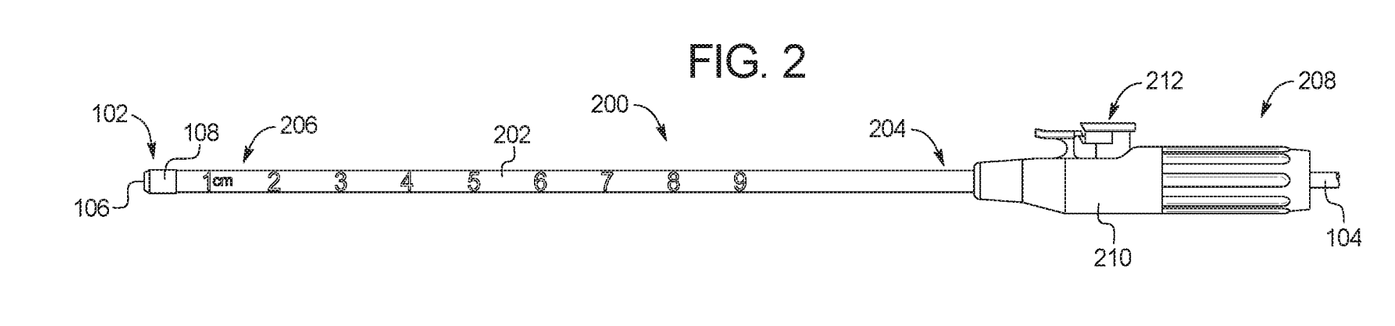
FIG. 2 is a perspective view of an example delivery probe, according to an example embodiment of the present disclosure.

FIG. 2 is a perspective view of an example delivery probe 200, according to an example embodiment of the present disclosure. The delivery probe 200 includes an elongated member 202, which has a proximal end 204 and a distal end 206, and a bridle lock 208. The elongated member 202 may be made of a flexible material (e.g., polyethylene) and may be approximately 5 inches long. For example, the elongated member 202 may include a flexible material which includes a construction of one or more materials including a coextruded stainless steel coil, polyethylene, silicon, thermoplastic, and the like, and may also be latex-free. In an example embodiment, the elongated member 202 has indices (e.g., 1 cm through 9 cm) to allow a clinician to easily see how far into the nasal cavity that the delivery probe 200 has been inserted. The bridle 104 extends through the elongated member 202 from the magnetic portion 102 through the bridle lock 208. The bridle lock 208 may be held by the clinician for insertion of the delivery probe 200 into a nostril. The bridle lock 208 includes a housing 210 and an actuator 212. The housing 210 may be approximately 2 inches long with approximately one half inch in diameter. Upon actuation of the actuator 212 by the clinician, the bridle lock 208 releases the bridle 104. As explained in further detail below, the bridle 104, which is illustrated in FIG. 2 as extending outward from the back of the housing 210, is held in place by the bridle lock 208 until the actuator 212 is actuated to release the bridle 104 which may then be pulled though both the bridle lock 208 and the elongated member 202 by the magnetic portion 102 into the nasal cavity.

Figure 3:
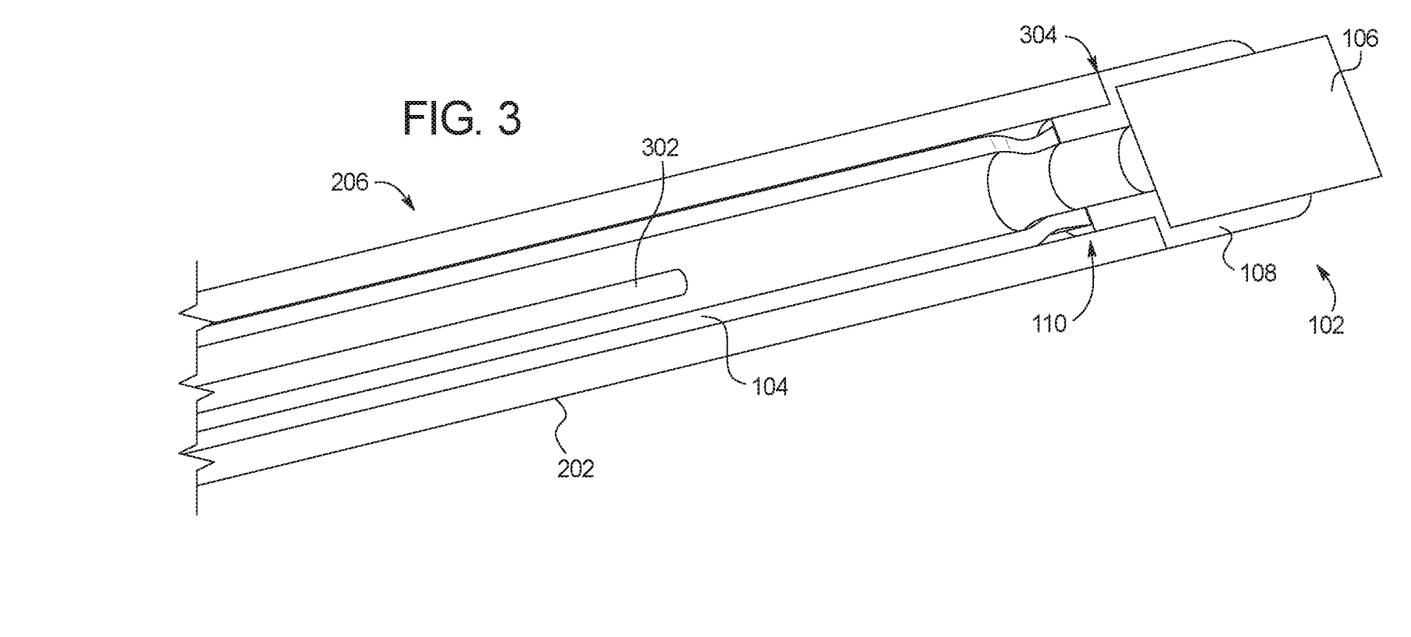
FIG. 3 is a cross-sectional view of an example delivery probe, according to an example embodiment of the present disclosure.

FIG. 3 is a cross-sectional view of an example delivery probe 200, according to an example embodiment of the present disclosure. As shown in FIG. 3, a stylet 302 may be included inside the elongated member 202. The stylet 302 adds rigidity to the elongated member 202, which helps with placement of the magnetic portion 102 near the rear of the vomer bone. The stylet 302 may be provided as a wire, braided wires, or any other suitable material, and may have a fixed length. The magnetic portion 102 is seated in and abuts the end of the distal portion 206 of the elongated member 200. While the bridle lock 208 is holding the bridle 104 in place, the magnetic portion 102 is held in place by tension on the bridle 104 (e.g., the bridle 104 is pulled taught between the bridle lock 208 and the end of the distal portion 206). When the bridle lock 208 releases the bridle 104, the magnetic portion 102 may release from the distal portion 206 of the elongated member 200 at disconnection point 304. When the magnetic portion 102 releases from the disconnection point 304, the bridle 104 may be pulled by the magnetic portion 102 around the vomer bone. As illustrated in FIG. 3, the bridle 104 may be curved around the interior of the elongated member 202 and around the stylet 302 in a semicircular shape and connect to the magnetic tip portion 108 at the connection point 110 in a curved manner. In an example embodiment, a coil wire (not illustrated) may extend around the elongated member 202 to provide some additional rigidity. It should be appreciated that the gauge of the wire and the pitch of the wire coils may vary to provide a suitable level of flexibility and rigidity.

Figure 4A:
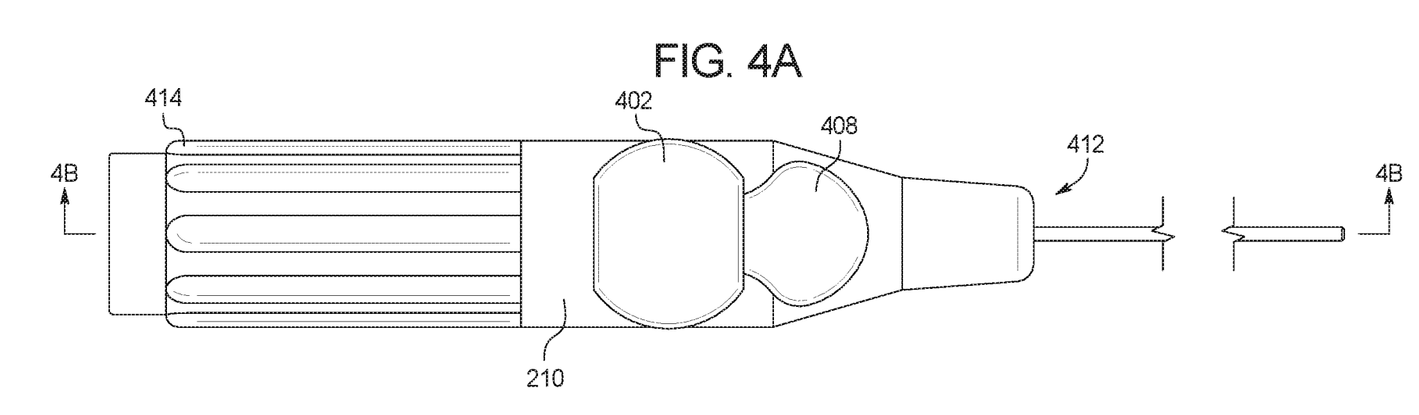
FIG. 4A is a top view of an example bridle lock, according to an example embodiment of the present disclosure.
Figure 4B:
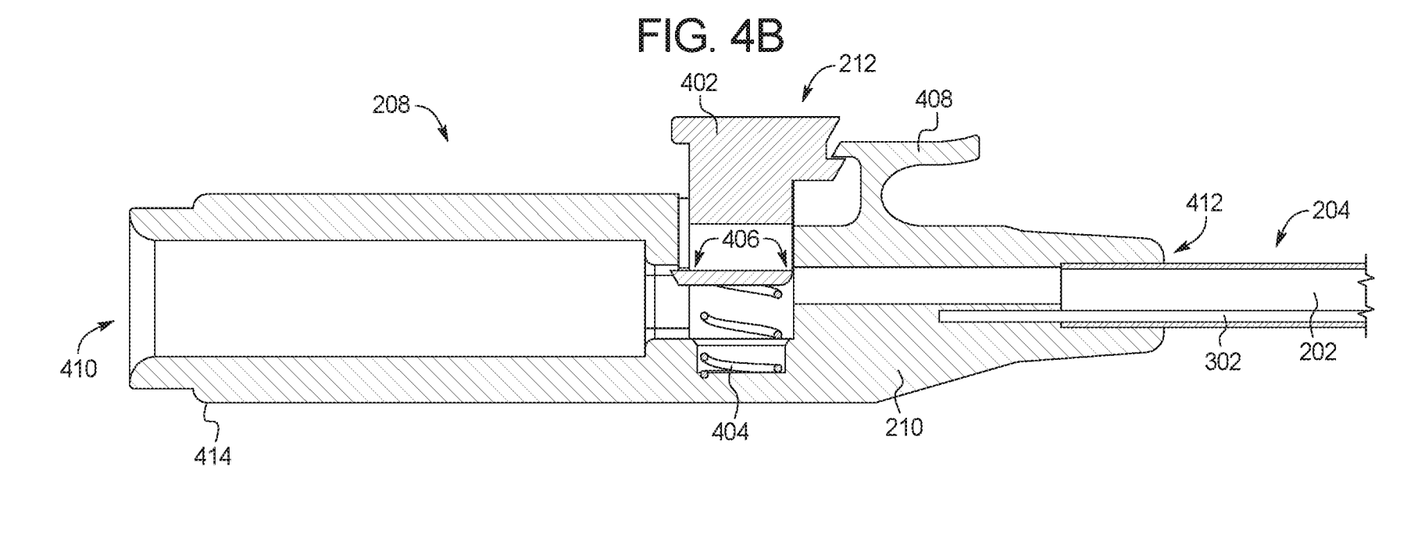
FIG. 4B is a cross-sectional view of an example bridle lock, according to an example embodiment of the present disclosure.

FIG. 4A is a top view of an example bridle lock 208, according to an example embodiment of the present disclosure, and FIG. 4B provides a cross-sectional view of the example bridle lock 208 taken along line 4B-4B of FIG. 4A. The actuator 212 includes, for example, a button 402, a spring 404, a crimping region 406, and a button control tab 408. The bridle lock 208 includes a bridle channel 410, a connection portion 412, and gripping members 414. The bridle channel 410 extends through the housing 210 and allows the bridle 104 to go through the bridle lock 208. The proximal end 204 of the elongated member 202 is seated in the connection portion 412 to connect the elongated member 202 to the bridle lock 208. A suitable adhesive or fastening mechanism may be used to connect the elongated member 202 into the connection portion 412. Also, the stylet 302 extends from the housing 210 through the connection portion 412 and into the elongated member 202. The gripping members 414 may be provided on the housing 210 to allow for improved grip and manipulation of the delivery probe 200.

The button 402 may be in a disengaged state (e.g., down) or an engaged state (e.g., up). In the engaged state, the bridle 104 is crimped between the button 402 and the housing 210 in the crimping region 406. The crimping region 406 provides enough force to not allow the bridle 104 to move without significant pulling force on the bridle 104, such that when the magnetic portions 102 and 508 make contact, the crimping region 406 does not release the bridle 104. However, when the button 402 is in the disengaged state, the bridle 104 can move freely through the crimping region 406. The button control tab 408 holds the disengaged button 402 down against the upward force of the spring 404. When the button control tab 408 is pressed, the button 402 engages by rising up to crimp the bridle 104 in the crimping region 406 when the spring 404 pushes the button 402 upwards. Accordingly, a clinician can advantageously hold the delivery probe 200 without having to hold the bridle 104 and/or the elongated member 202 during the entire process of inserting the delivery probe 200. Thus, there is a reduction in the risk of the magnetic portion 102 and bridle 104 unintentionally releasing in a premature fashion, which can be a cause of clinician inefficiency and increases in cost of care. It should be appreciated that it may be difficult for a clinician to articulate the placement of a delivery probe while simultaneously holding a bridle and/or an elongated member, particularly when wearing gloves, holding other items in their hands, and working in a stressful environment. The bridle lock 208 allows the clinician to avoid a premature release of the magnetic portion 102 and the bridle 104. Furthermore, the bridle lock 208 allows for the delivery probe 200 to include additional curvature at the distal end 206 of the elongated member 202, which may be done at the clinician's discretion (e.g., if the clinician pulls the bridle 104 back through bridle lock 208, increasing the tension between the crimping region 406 and the connection point 110 and the distal end 206 of the elongated member 202). Accordingly, the increased tension may cause a pronounced curvature between the end of the stylet 302 and the connection point 110, which may aid in providing for an optimal magnetic coupling between magnetic portions 102 and 508. The stylet 302 may have a fixed length or may be configured to have different lengths. Further, in an example embodiment, the actuator 212 may be a twist actuator, similar to a twist retractable pen. Moreover, the bridle lock 208 may include any suitable actuator 212, including a toggle switch, rotary switch, etc. Also, the button 402 may alternatively crimp the bridle 104 when the button 402 is down or depressed, and allow the bridle 104 to move freely when the button 402 is up or not depressed. Any suitable means of actuation for allowing the bridle 104 to move freely in a first state and stopping the bridle 104 from moving freely in a second may be utilized.

Figure 5A:
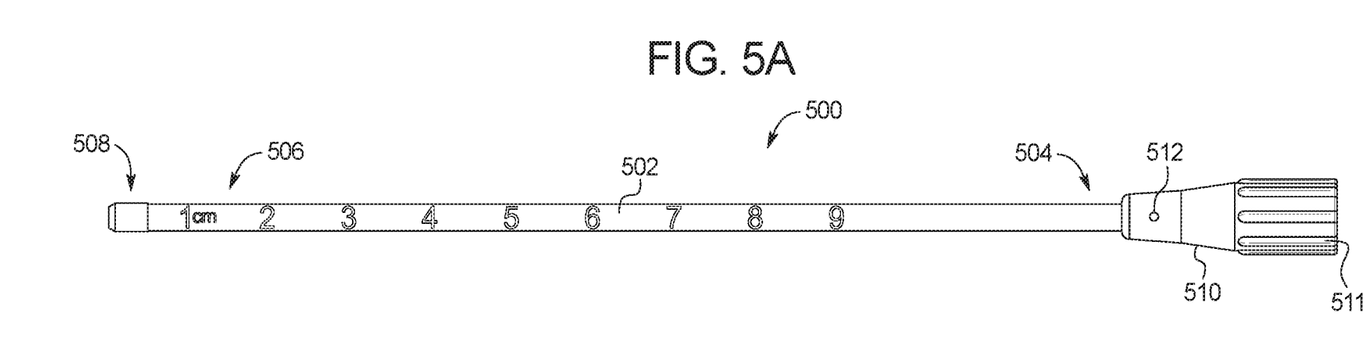
FIG. 5A is a perspective view of an example retrieval probe, according to an example embodiment of the present disclosure.
Figure 5B:
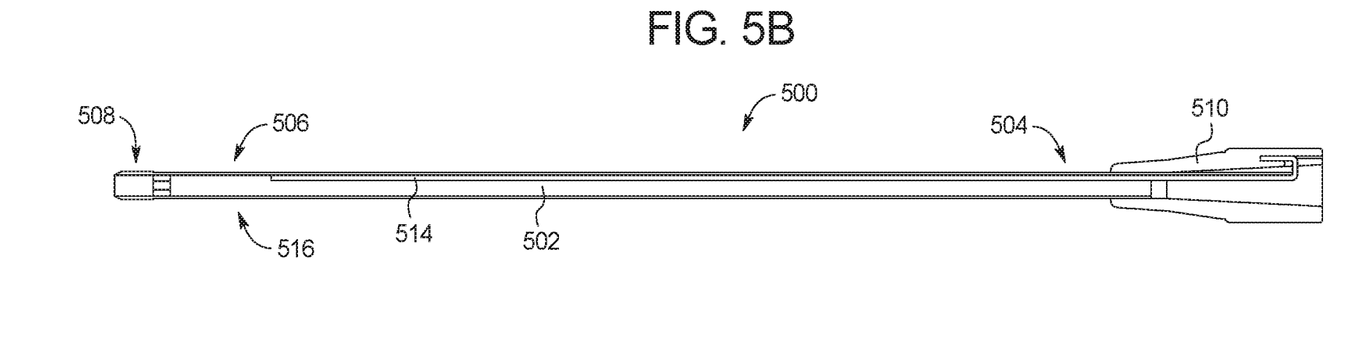
FIG. 5B is a cross-sectional view of an example retrieval probe, according to an example embodiment of the present disclosure.

FIG. 5A is a top view of an example retrieval probe 500, according to an example embodiment of the present disclosure, and FIG. 5B provides a cross-sectional view of the example retrieval probe 500. The retrieval probe 500 includes elongated member 502, which has a proximal end 504 and a distal end 506, a magnetic portion 508, a handle portion 510, a magnetic coupling indicator 512, and a stylet 514. The elongated member 502 of the retrieval probe may be approximately 5 inches long, with the handle portion 510 being approximately one inch long. The retrieval probe 502 may include certain features similar to the above discussed delivery probe, for example, as illustrated in FIGS. 5A and 5B. For example, the elongated member 502 may include indices (e.g., 1 cm through 9 cm) to allow a clinician to easily see how far into the nasal cavity that the retrieval probe 500 has been inserted. Typically, unlike the releasable magnetic portion 102, the magnetic portion 508 would be permanently attached to the distal end 506 of the elongated member 502. In an example embodiment, the magnetic portion 508 includes a rare earth magnet, or any suitable magnetic member to provide for magnetic coupling between the delivery probe 200 and the retrieval probe 500. The handle portion 510 may be smaller than the bridle lock 208, or may be similarly sized. Similarly, a suitable adhesive or fastening mechanism may be used to connect the elongated member 502 to the handle portion 510. Gripping members 511 may also be included on the handle portion 510 for ease of use.

The magnetic coupling indicator 512 may be a light emitting diode. A magnetic coupling indicator may be any suitable indicator, such as an audible indicator, visual indicator, haptic indicator, or the like. Also, a magnetic coupling indicator 512 may be located in nearby equipment and wirelessly receive signals from the retrieval probe 500 to provide an indication of magnetic coupling. In an example embodiment, the delivery probe 200 may include a magnetic coupling indicator 512. The stylet 514 may be provided within the elongated member 502 and anchored into the handle portion 510. In an example embodiment, the stylet 514 does not extend the full length of the elongated member 502 which may provide a region 516 of increased flexibility at the distal end 506. This advantageously allows the magnetic portions 102 and 508 to more easily engage with full on face to face contact. In an example embodiment, the stylet 514 may be inserted into the elongated member 502 to variable lengths, for example, by pulling the stylet 514 out of the handle portion 510, or using any suitable mechanism to move or extend the stylet towards or away from the distal end 506 of the elongated member 502. Likewise, in an example embodiment, the stylet 302 may be adjustable to various lengths within the elongated member 202. Also, similar to the above discussed clinician articulation of the delivery probe 200 using the bridle 104 tensioned with the bridle lock 208, the retrieval probe 500 may include, inside the elongated member 502, a tensioning member similar to the bridle 104 and a locking mechanism similar to the bridle lock 208. Accordingly, for example, a clinician may articulate both the delivery probe 200 and the retrieval probe 500 to have a pronounced curvature at the distal end of the elongated members 202, 502, according to applied tension and/or stylet length, to aid in achieving an optimal magnetic coupling between magnetic portions 102 and 508.

Figure 6A:
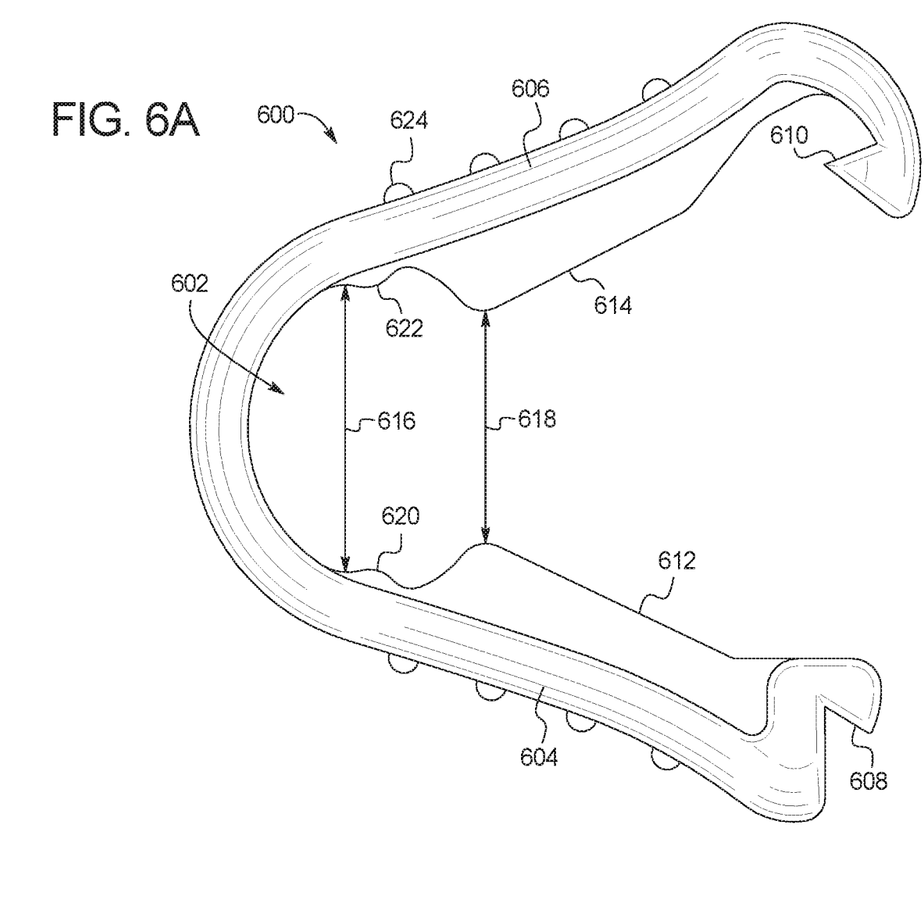
FIG. 6A is a perspective view of an example clamp, according to an example embodiment of the present disclosure.
Figure 6B:
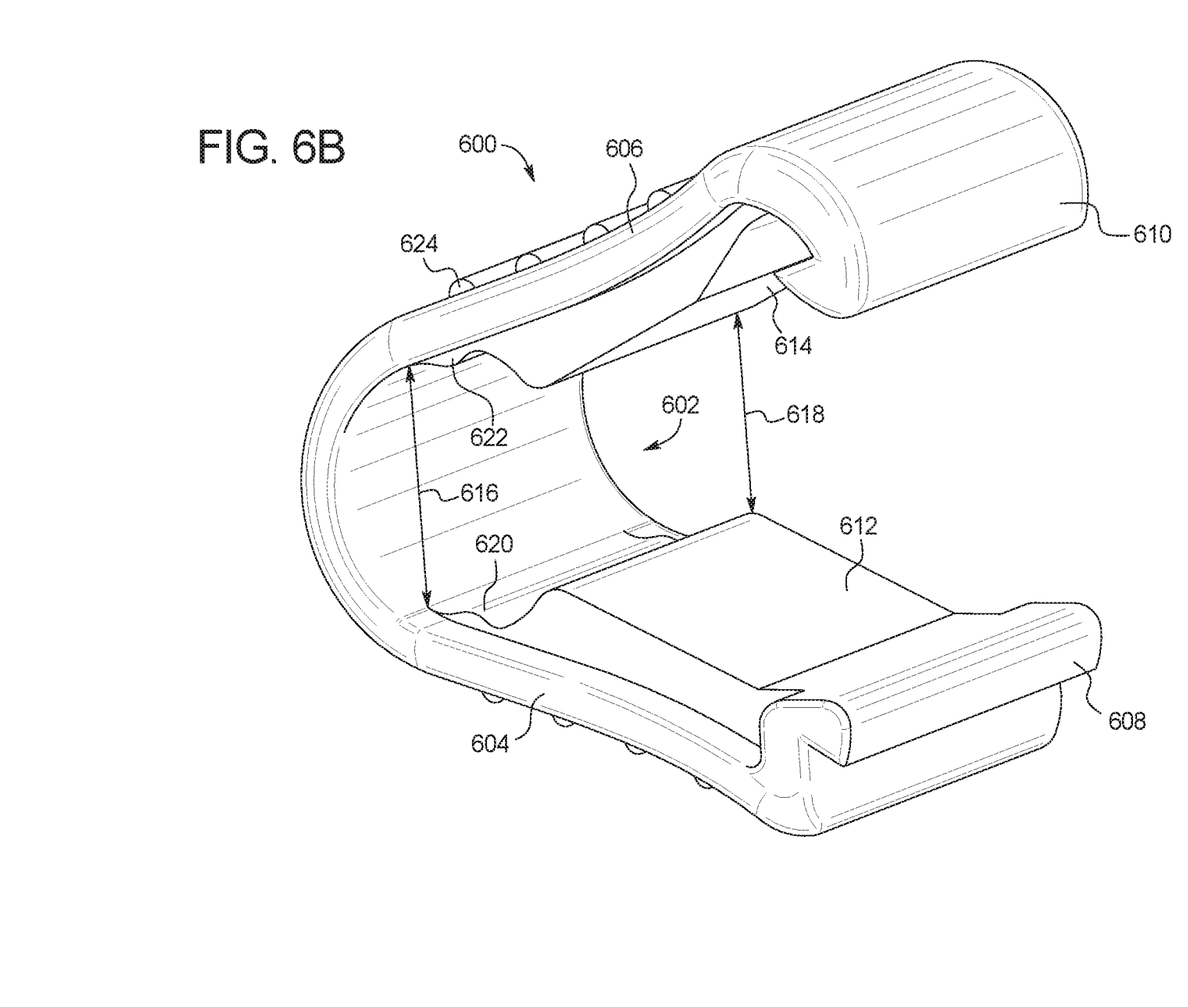
FIG. 6B is a perspective view of an example clamp, according to an example embodiment of the present disclosure.
Figure 6C:
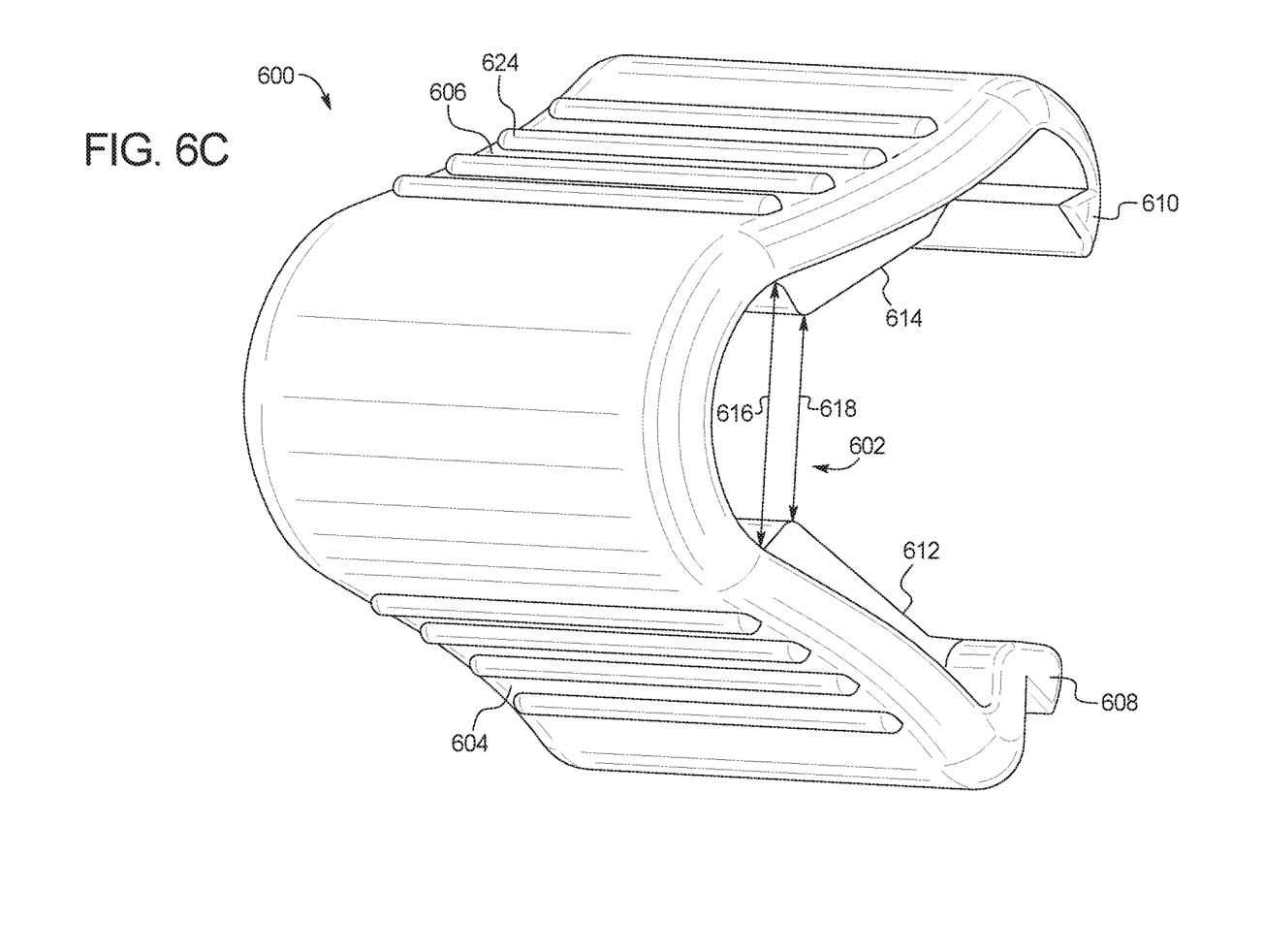
FIG. 6C is a perspective view of an example clamp, according to an example embodiment of the present disclosure.

FIG. 6A is a perspective view of an example clamp 600, according to an example embodiment of the present disclosure, and FIGS. 6B and 6C provide additional perspective views of the example clamp 600 from alternate viewpoints. As illustrated in FIGS. 6A, 6B, and 6C, the clamp 600 includes a channel portion 602, extending portions 604, 606, clamping portions 608, 610, and flat faces 612, 614. The extending portions 604, 606 are located on opposing sides of the channel portion 602. Likewise, the clamping portions 608, 610, and flat faces 612, 614 are also located on opposing sides of the channel portion 602. A nasal tube may be inserted into the channel portion 602 along with the bridle 104, and upon closing the clamp 600, the nasal tube is secured in place with the bridle 104. The channel portion 602 includes an inside diameter 616, which is larger than an outside diameter of a nasal tube to be secured in the clamp 600, when the clamp 600 is in an open position as shown in FIGS. 6A, 6B, and 6C. Also, the clamp 600 includes an internal clearance 618 between the extending portions 604, 606, pressure bars 620, 622, located on opposing extending portions 604, 606, and gripping members 624. The clamping portions 608, 610 may include any suitable clamping mechanism for maintaining the extending portions 604, 606 together. The flat faces 612, 614 may provide structural support for the clamp 600 in a closed position, and may support proper engagement of the clamping portions 608, 610. In an example embodiment, the flat faces 612, 614 include a textured surface or gripping members, which may aid in clamping the bridle 104. The pressure bars 620, 622 provide an increased level of precision in setting a pressure level that is exerted on the nasal tube while the clamp 600 is closed. The gripping members 624 allow the clinician to easily manipulate the clamp 600.

As illustrated in FIGS. 6A, 6B, and 6C, the example clamp 600 is a single piece, which may be molded plastic. The clamp 600 does not include a hinge to close, rather, the inside diameter 616 of the channel portion 602 decreases as the extending portions 604, 606 are pressed towards each other. When the clamping portions 608, 610 are engaged, the inside diameter 616 of the channel portion 602 is less than the outside diameter of the nasal tube, such that the nasal tube may be secured. It should be appreciated that various sizes of clamps 600 may be made to accommodate various different sizes of nasal tubes. In an example embodiment, the nasal tube is a size 10 FR, and the clamp 600 may indicate the matching size, 10 FR. Accordingly, the inside diameter of the clamp 600, for example as best shown in FIG. 6A or 6C, in the open state, is greater than the nasal tube and likewise, the internal clearance 618 is greater than or substantially equal to the outside diameter of the size 10 FR nasal tube. It should be appreciated that the internal clearance 618 is substantially equal to the outside diameter of the nasal tube if only minimal pressing force is required to seat the nasal tube in the channel portion 602. Accordingly, the clinician can advantageously place the clamp 600 onto the nasal tube without having to smash the nasal tube through the internal clearance 618 and into the channel portion 602 of the clamp 600. Accordingly, the clamp 600 decreases the chance of dropping the clamp or other items when placing the nasal tube into the channel region 602. Once the clamp 600 is placed onto the nasal tube, the clamp 600 may just hang on the nasal tube, as the center of gravity of the clamp 600 causes the extending portions 604, 606 to swing downward, keeping the channel portion 602 seated on the nasal tube, while advantageously allows the clamp 600 to freely slide along the nasal tube. This may provide for significantly improved placement of the clamp 600, resulting in improved securing of the nasal tube. Specifically, if the inside diameter of a clamp is smaller than the outside diameter of the nasal tube, it is difficult to slide the clamp along the nasal tube. Proper placement of the clamp 600 is important because poor placement may be annoying to the patient and may lead to various other undesirable outcomes as further discussed below. For example, a patient may intentionally or accidentally pull on the bridle 104, particularly if the clamp 600 is placed with too far away from the nostril. For example, something may become hooked into the bridle 104 or between the nasal tube and the clamp. Pulling on the bridle 104 can damage the tissue and vomer bone, and can be very painful. Furthermore, the pressure bars 620, 622 may apply an inward pressure onto the nasal tube so that, with a pulling force of, for example, 2 to 10 pounds, the nasal tube will deform and become thin enough to slowly slide through the clamp 600. It should be appreciated that the nasal tube should not slip through the channel portion too easily, as the nasal tube may become displaced. However, on the other hand, there may be instances where it is desirable to intentionally move the nasal tube through the clamp without opening the clamp. The pressure bars 620, 622 advantageously allow for increased precision in allowance of movement at a specific level of force. In an example embodiment, the pressure bars 620, 622 apply a force requiring 4 to 6 pounds of pulling force to move the clamp 600 along the nasal tube. Also, when the clamp 600 is in the closed position, disengaging the clamping portions 608, 610 may require a threshold force. Various means for disengaging the clamping portions 608, 610 may by used (e.g., fingernail, toothpick). In an example embodiment, using a guitar pick to open the clamp 600 may advantageously reduce risk of injury to a patient and/or a clinician. Accordingly, the presently disclosed clamp advantageously avoids many potentially problematic issues associated with clamping and securing a nasal tube.

Figure 7:
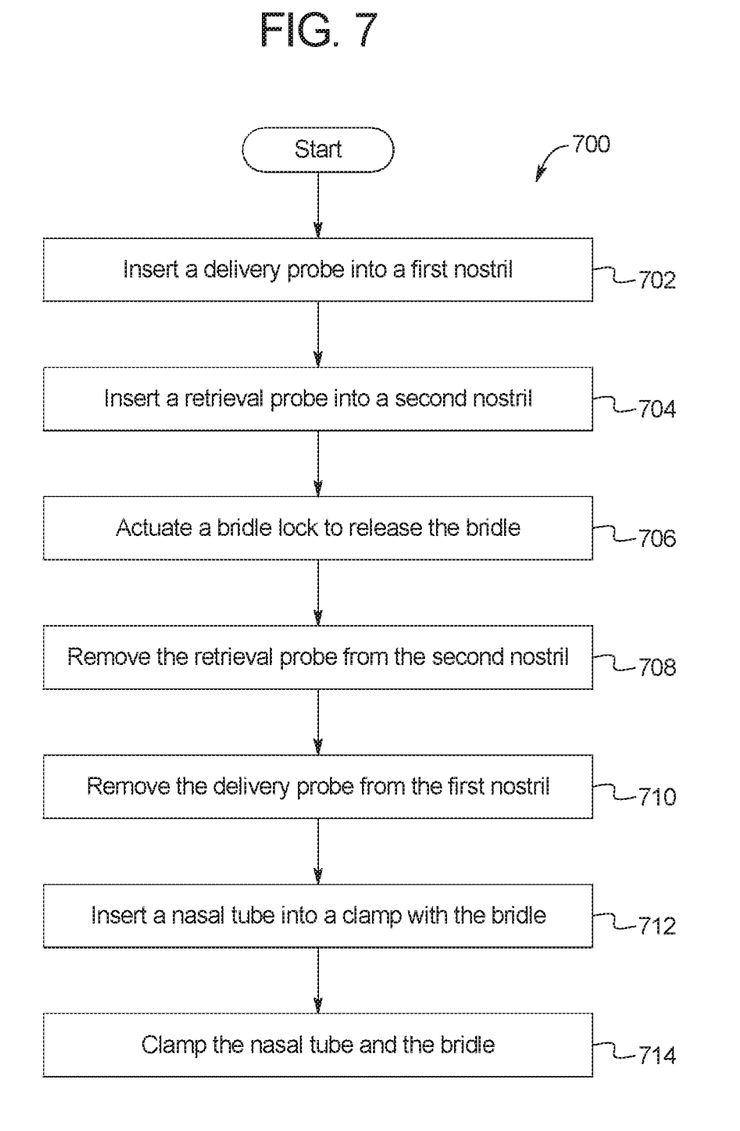
FIG. 7 includes a flowchart illustrating an example process for securing a nasal tube, according to an example embodiment of the present disclosure.

FIG. 7 includes a flowchart of an example process 700 for securing a nasal tube. Although the process 700 is described with reference to the flowchart illustrated in FIG. 7, it will be appreciated that many other methods of performing the acts associated with the process 700 may be used. For example, the order of many of the blocks may be changed, many blocks may be intermittently repeated or continually performed, certain blocks may be combined with other blocks, and many of the blocks described are optional or may only be contingently performed.

The example process 700 may begin with a clinician inserting a delivery probe into a first nostril (block 702). Then, a retrieval probe is inserted into a second nostril (block 704). For example, the magnetic portion 102 of the delivery probe 200 and the magnetic portion 508 of the retrieval probe are both inserted towards the rear of the vomer bone of a patient through the patient's right and left nostrils, which causes a magnetic coupling of the magnetic portions 102 and 508. The clinician may see an LED indicator turn on when the magnetic coupling occurs. Then, an actuation of a bridle lock 208 releases the bridle 104 (block 706). For example, the clinician presses an actuator 212 (e.g., a button) to release the bridle 104 to allow the magnetic portion 102 and the bridle 104 to slide around the vomer bone. The retrieval probe 500 is removed from the second nostril, such that the bridle 104 extends into the first nostril and out from the second nostril (block 708). The delivery probe 200 is removed from the first nostril (block 710). For example, the retrieval probe 500 pulls the bridle 104 out through the second nostril and pulls the delivery probe 200 out of the first nostril, leaving the bridle 104 hanging out of both nostrils. A nasal tube is inserted into a clamp 600 with the bridle 104 (block 712). For example, the clamp 600 is placed onto the nasal tube (e.g., below the mouth) and the channel portion 602 slid into a proper position for securing the nasal tube, near the nostril so as to not be in the way of the patient's mouth. The clamp 600 easily slides to the proper position because the outside diameter of the nasal tube is smaller than the inside diameter of the channel portion 602 when the clamp 600 is in the open position. The nasal tube and the bridle 104 are clamped in the clamp 600 (block 714). For example, having the clamp placed near the nostril, the nasal tube is clamped with the bridle 104 by pressing the clamp 600 together. Accordingly, the nasal tube is secured using the above disclosed method.

In view of the above disclosure, the presently disclosed systems, methods, and apparatus may advantageously provide for improved outcomes, efficiency, patient comfort, etc. in comparison to the existing systems in the art. For example, an advantageously low amount of drag occurs in pulling the bridle 104 through the nostrils and around the vomer bone, without requiring any long flexible tube to be dragged with the magnetic portion 102, and potentially get kinked, requiring an even greater pulling force to unkink and drag the long flexible tube through. Also, an optimal magnetic coupling is highly likely to occur using the presently disclosed system, as opposed to systems which do not have probes that may provide additional curvature at the distal end to allow for bending around the vomer bone, possibly resulting in failed attempts to place a bridle. A clinician can advantageously maneuver the delivery probe 200 without worrying about continuously holding on the bridle 104 or the elongated member 202 to ensure that the magnetic portion 102 does not prematurely release, and can easily release the bridle 104 and magnetic portion 102 by pressing a button 402. Also, the nasal tube can be easily placed in the clamp 600, which is easily slid into place, resulting in a simpler, safer, and hassle-free securing of the nasal tube. Specifically, for example, it should be appreciated that placing a nasal tube, prior to securing the nasal tube, may involve using a sophisticated device position tracking system for positioning the tip of the nasal tube into a specific location within the body. For example, the tip of nasal tube may need to be placed in the duodenum, rather than in the stomach, which generally requires that a clinician needs to work the tip of the nasal tube through the pylorus. This typically requires significant effort, generally requiring the use of sophisticated equipment including, for example, a tubing assembly with a precisely located positioning device, an external device that detects the positioning device, a display for tracking the position of the tip of the nasal tube, etc., as described in further detail in: "Catheter Locator Apparatus And Method Of Use," filed on Dec. 23, 2009, as U.S. patent application Ser. No. 12/646,263, issued on Sep. 11, 2012, as U.S. Pat. No. 8,265,732; "Catheter Locator Apparatus And Method Of Use," filed on Aug. 9, 2012, as U.S. patent application Ser. No. 13/570,999; "Tubing Assembly And Signal Generator Placement Control Device And Method For Use With Catheter Guidance Systems," filed on Jan. 13, 2005, as U.S. patent application Ser. No. 11/036,514, issued on Jul. 12, 2011, as U.S. Pat. No. 7,976,518; and "Tubing Assembly And Signal Generator Placement Control Device And Method For Use With Catheter Guidance Systems," filed on Jun. 2, 2011, as U.S. patent application Ser. No. 13/151,882, the entire contents of each of which are incorporated by reference herein. The use of such equipment and associated clinician time incurs significant costs. Once the tip of the nasal tube is properly placed in the duodenum, it is very important that the tip of the nasal tube is not pulled back through the pylorus, out of the duodenum, and into the stomach. A typical scenario in which this problematic event may occur is when a clinician is trying to clamp the nasal tube, and the clinician accidentally pulls the nasal tube out a small distance to create enough space to place the nasal tube into a clamp at the proper location, thereby unintentionally removing the tip of the nasal tube from the duodenum, through the pylorus, and into the stomach. In such a scenario, the clinician may not realize that the tip of the nasal tube has traversed the pylorus. Accordingly, a very serious risk is presented, in that the patient may experience aspiration of fluid from excess fluid in the stomach, which may lead to fluid in the lungs, causing negative outcomes including pneumonia or death by asphyxiation. Thus, the presently disclose clamp 600 advantageously reduces the above described risks associated with unintentional movement of an already placed nasal tube during the process of securing the nasal tube. Accordingly, great improvements in patient safety, patient outcomes, clinician efficiency, and medical costs, may be achieved using the presently disclosed system, method, and apparatus for securing nasal tubes.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Also, it should be appreciated that the features of the dependent claims may be embodied in the systems, methods, and apparatus of each of the independent claims.

The invention is claimed as follows:

1. A system for securing a nasal tube, the system comprising:
   a bridle;
   a first magnetic portion integrally attached to the bridle;
   a delivery probe including:
     a first elongated member having a first proximal end and a first distal end, the first distal end being configured to deliver the first magnetic portion, wherein the first magnetic portion is releasable, wherein the first magnetic portion includes a magnet and a magnet holding tip, wherein the magnet has an overall width that is less than an overall width of the magnet holding tip inside which the magnet is held, further wherein a width of the bridle curves around a bottom of the magnetic holding tip at a connection point;
   a retrieval probe including:
     a second elongated member having a second proximal end and a second distal end, the second distal end including a second magnetic portion configured to magnetically couple with the first magnetic portion; and
     a magnetic coupling indicator configured to provide an indication in response to the first magnetic portion and the second magnetic portion being magnetically coupled; and
   a clamp including a channel portion with an inside diameter larger than an outside diameter of the nasal tube, the clamp configured to secure the nasal tube.

2. The system of claim 1, wherein the first elongated member is a catheter.

3. The system of claim 1, wherein the first elongated member includes a stylet, and the first elongated member is a first length from the first proximal end to the first distal end, and the stylet extends from the first proximal end toward the first distal end for a second length which is less than the first length.

4. The system of claim 3, wherein the first elongated member is configured to adjustably curve over a third length of the first elongated member beyond the second length when a tension is applied to the bridle.

5. The system of claim 1, wherein at least one of the first elongated member and the second elongated member is a flexible tube.

6. The system of claim 1, wherein at least one of the first elongated member and the second elongated member includes an integrally formed coil.

7. The system of claim 1, wherein at least one of the first elongated member and the second elongated member includes a stylet.

8. The system of claim 7, wherein the stylet is configured to be adjusted to varying lengths.

9. The system of claim 1, wherein a magnetic coupling of the first magnetic portion and the second magnetic portion is a face to face magnetic coupling.

10. The system of claim 1, wherein at least one of the first magnetic portion and the second magnetic portion includes a rare earth magnet.

11. The system of claim 1, wherein at least one of the first magnetic portion and the second magnetic portion includes a permanent magnet.

12. The system of claim 1, wherein at least one of the first magnetic portion and the second magnetic portion includes at least one of a cylindrical magnet and a ring magnet.

13. The system of claim 1, wherein the first magnetic portion is inflexible.

14. The system of claim 1, wherein the second magnetic portion is permanently attached to the second distal end of the second elongated member.

15. The system of claim 1, wherein the first magnetic portion is over-molded to include a portion of the bridle.

16. The system of claim 1, wherein the delivery probe includes a magnetic coupling indicator configured to provide an indication in response to the first magnetic portion and the second magnetic portion being magnetically coupled.

17. The system of claim 16, wherein the magnetic coupling indicator of the delivery probe or the receiving probe is a light emitting diode.

18. The system of claim 1, wherein the clamp is a hingeless monolithic clamp.

19. The system of claim 1, wherein the clamp includes two pressure bars on opposing sides of the channel portion.

20. The system of claim 1, wherein a minimum clearance between opposing sides of the clamp is greater than or substantially equal to an outside diameter of the nasal tube.

21. A system for securing a nasal tube, the system comprising:
   a bridle;
   a first magnetic portion connected to the bridle, wherein the first magnetic portion is releasable, wherein the first magnetic portion includes a magnet and a magnet holding tip, wherein the magnet has an overall width that is less than an overall width of the magnet holding tip inside which the magnet is held, further wherein the width of the bridle curves around the bottom of the magnetic holding tip at a connection point;
   a delivery probe including:
     a first elongated member having a first proximal end and a first distal end, the first distal end being configured to deliver the first magnetic portion, wherein the first magnetic portion is configured to be seated within the first distal end of the first elongated member; and
   a retrieval probe including a second elongated member having a second proximal end and a second distal end, the second distal end including a second magnetic portion configured to magnetically couple with the first magnetic portion.

22. A method for securing a nasal tube, the method comprising:
   inserting a delivery probe into a first nostril, the delivery probe including a first elongated member having a first proximal end and a first distal end, the first distal end being configured to deliver a first magnetic portion which is connected to a bridle, wherein the first magnetic portion is configured to be seated within the first distal end of the first elongated member, wherein the first magnetic portion is releasable, wherein the first magnetic portion includes a magnet and a magnet holding tip, wherein the magnet has an overall width that is less than an overall width of the magnet holding tip inside which the magnet is held, further wherein a width of the bridle curves around a bottom of the magnetic holding tip at a connection point;

inserting a retrieval probe into a second nostril, the retrieval probe including a second elongated member having a second proximal end and a second distal end, the second distal end including a second magnetic portion configured to magnetically couple with the first magnetic portion;

releasing the bridle;

removing the retrieval probe from the second nostril and the delivery probe from the first nostril, such that the bridle extends into the first nostril and out of the second nostril;

inserting the nasal tube into a clamp with the bridle; and clamping the nasal tube and the bridle.

23. The method of claim 22, wherein the bridle is released in response to a magnetic coupling indicator providing an indication in response to the first magnetic portion and the second magnetic portion being magnetically coupled.

24. The method of claim 22, wherein the clamp includes a channel portion with an inside diameter larger than an outside diameter of the nasal tube.

25. The method of claim 24, further comprising:

sliding the channel portion along the nasal tube into a first position before clamping the nasal tube and the bridle.

\* \* \* \* \*